United States Patent [19]

Wright et al.

[11] Patent Number: 5,413,784
[45] Date of Patent: May 9, 1995

[54] BIOPESTICIDE COMPOSITION AND PROCESS FOR CONTROLLING INSECT PESTS

[76] Inventors: James E. Wright, 5006 Oakmont Cir., Harlingen, Tex. 78552; Laurence D. Chandler, 4003 Royce Rd., Tifton, Ga. 31794

[21] Appl. No.: 58,795

[22] Filed: May 10, 1993

Related U.S. Application Data

[63] Continuation of Ser. No. 892,488, Jun. 3, 1992, which is a continuation of Ser. No. 638,489, Jan. 9, 1991, abandoned.

[51] Int. Cl.⁶ .................... A01N 63/04; C12N 1/14
[52] U.S. Cl. .................. 424/93.5; 435/254.1; 424/84; 426/1
[58] Field of Search .............. 424/93 Q; 71/316; 435/254.1

[56] References Cited

U.S. PATENT DOCUMENTS

| | | | |
|---|---|---|---|
| 3,657,414 | 4/1972 | Hedin | 424/93 |
| 3,895,078 | 7/1975 | Gueldner et al. | 424/84 |
| 4,027,420 | 6/1977 | McKibben et al. | 43/124 |
| 4,293,552 | 10/1981 | Miesel | 514/255 |
| 4,337,271 | 6/1982 | Jacobson | 514/578 |
| 4,348,385 | 9/1982 | Synek | 514/80 |
| 4,751,082 | 6/1988 | Schaerffenberg et al. | 424/93 Q |
| 4,797,276 | 1/1989 | Herrnstadt et al. | 424/84 |
| 4,908,977 | 3/1990 | Foster | 43/107 |
| 4,925,663 | 5/1990 | Stimac | 424/93 Q |
| 4,942,030 | 7/1990 | Osborne | 424/93 R |
| 5,057,316 | 10/1991 | Gunner et al. | 424/93 |

OTHER PUBLICATIONS

A. H. Treifi, "Use of *Beauveria bassiana* (Bais) to Control the Immature Stages of the Whitefly *Trialeurodes vaporarium* (Westw.) (Homoptera:Aleyrodidae) in the greenhouse", *Arab Journal of Plant Protection 1984*, 2(2):83–86 (Arabic) (English Abstract only).

J. Dirlbek et al., "Management of Gerbera Protection Against Glasshouse Whitefly *Trialeurodes-vaporarium* Westw"; *SB Uvtiz (Ustav Vedeckotech inF ZemED) Ochr Rostl* 25(4), pp. 289–298, 1989 (in Czech with English summary) (Also providing English abstract).

O. A. Aleshina, "The Status and Prospects for the Study of Entomo Pathogenis Fungi in the USSR", *Mikologiya Filopatologiya* 12(6), pp. 457–460, 1978 (rec'd 1979) (Russian) (Also providing English abstract).

F. Y. Yarkulow, "The Biological Method in Greenhouse in the Maritime Territory", *Zashchita Rastenii*, No. 12, pp. 20–21, 1986 (Russian) (Also providing English abstract).

J. Dirlbek et al., "Greenhouse Whitefly Management Based on Short-term Forecasting and Warning", Proceedings of the XI Czechoslovak Plant Protection Conference in Nitra Sep. 6–8, 1988, pp. 131–132 (Czech with English summary) (Also providing English abstract).

G. A. Beglyarov et al., "Toxicity of Some Pesticides for Encarsia", *Zashchita Rastenii* (Moscow) No. 11, pp. 36–37, 1978 (Russian) (Also providing Chem. Abstract thereof, i.e. CA:90(17)133954u).

(List continued on next page.)

*Primary Examiner*—Jacqueline Stone
*Attorney, Agent, or Firm*—Banner, Birch, McKie and Beckett

[57] ABSTRACT

The subject invention concerns a novel and useful biopesticide with activity against insect pests such as boll weevil, sweet potato whitefly and cotton fleahopper. The biopesticide of the subject invention comprises an entomopathogenic fungus having virulence against a targeted insect pest(s), an arrestant and feeding stimulant for the targeted insect pest(s) and, optionally, a pheromone for the targeted insect pest(s). A preferred fungus is a *Beauveria bassiana*, preferably *Beauveria bassiana*, ATCC-74040 (ARSEF-3097). By using this novel fungus, or mutant thereof, in the composition of the present invention, Boll weevils, sweet potato whiteflies and cotton fleahoppers can be controlled without environmental and public safety hazards presented by chemical control agents.

15 Claims, No Drawings

OTHER PUBLICATIONS

B. A. Borisov, "Increasing the Effectiveness of Entomopathogenic Fungi", *Zashchita Rastenii*, No. 9, pp. 20–22, 1983 (Russian) (Also providing English abstract).

G. A. Beglyarov et al., "Preference for the biological method;" *Zashchita Rastenii*, No. 7, pp. 14–15, 1984 (Russian) (Also providing English abstract).

T. I. Sukhova, "The Biological Method in the Greenhouse", *Zashchita Rastenii*, No. 2. pp. 37–38, 1987 (Russian) (Also providing English abstract).

V. B. Khamukov, "We are Extending Utilization of the Biological Method", *Zashchita Rastenii* (Moskva), No. 4, pp. 30–31, 1987 (Russian) (Also providing English abstract).

C. W. McCoy, "Engomogenous Fungi as Microbial Pesticides", New Directions in Biological Control:Alternatives for Suppressing Agricultural Pests and Diseases (Colloquium, Frisco, Colorado, U.S.A., Jan. 20–27, 1989), pp. 139–159, ©1990 Alan R. Liss, Inc., N.Y., N.Y.

S. G. Lisansky, "Microbial Insecticides", 1985 BCPC Mono, No. 32 Biotechnology and Its Application to Agriculture, pp. 145–151, Proceedings Sep. 4–6, 1985.

N. A. Filippov, "The Present State and Future Outlook of Biological Control in the USSR", *Acta Entomologica Fennica* 53:11–18, 1989.

*Microbial Control of Insects and Mites*, Edited by H. D. Burges and N. W. Hussey, Academic Press Inc. (London) Ltd., ©1971, Ch. 14 (by George Benz), pp.327–355.

*Microbial Control of Pests and Plants Diseases 1970–1980*, Edited by H. D. Burges, Academic Press Inc. (London) Ltd., ©1981, Ch. 17 (by C. M. Ignoffo et al.), pp. 329–362.

N. S. Avidzba, "Bioecology of Citrus Whitefly and its Integrated Management", *10th International Congress of Plant Protection 1983*, vol. 3, p. 1031 (Proceedings of a conference held at Brighton, England, Nov. 20–25, 1983).

T. W. Thomas et al., Agricultural Pest Management—Industry Report No. 938484, Tables 2 and 3, Author D. Little, Decision Resources, Incorporated, May 1, 1987 (from database printout).

M. F. Potter et al., "Field Persistence of Elcar ® (*Barculovirus heliothis*) Applied in a Bait Formulation for Control of Tobacco Budworm in Arizona Cotton", *J. Agric. Entomol.*, 1(1):78–81 (Jan. 1984).

M. R. Bell et al., "Microbial Control of Heliothis Spp. (Lepidoptera:Noctuidae) in Cotton: Dosage and Management Trials," *J. Entomol. Sci.*, 20(2):146–151 (Apr. 1985).

M. R. Bell et al., "Tobacco Budworm Field Evaluation of Microbial Control in Cotton Using *Bacillus thuringiensis* and Nuclear Polyhedrosis Virus with a Feeding Adjuvant," *J. Economic Entonmol.*, vol. 73, No. 3, pp. 427–430 (Jun. 1980).

M. F. Potter, "Laboratory and Greenhouse Performance of *Baculovirus heliothis*, Combined with Feeding Stimulants for Control of Neonate Tobacco Budworm," *Protection Ecology*, 5 (1983) pp. 161–165.

M. R. Bell, "Field Tests of a Nuclear Polyhedrosis Virus in a Bait Formulation for Control of Pink Bollworms and Heliothis spp. in Cotton in Arizona," *J. Economic Entomol.*, vol. 70, No. 5, pp. 625–629 (Oct. 1977).

M. R. Bell et al., "Tobacco Budworm: Development of a Spray Adjuvant to Increase Effectiveness of a Nuclear Polyhedrosis Virus," *J. Economic Entomol.*, vol. 71, No. 2, pp. 350–352 (Apr. 1978).

Tumlinson et al., "Sex Pheromones Produced by Male Boll Weevil: Isolation, Identification, and Synthesis," *Science*, vol. 166, No. 3908, pp. 1010–1012, (Nov. 12, 1969).

D. D. Hardee et al., "Boll Weevils in Nature Respond to Grandlure, A Synthetic Pheromone", *Journal of Economic Entomology*, vol. 65, No. 1, pp. 97–100 (Feb. 1972).

*Fungal Control of Insects*, published by F. G. Maxwell et al., "An Arrestant and Feeding Stimulant for the Boll Weevil in Water Extracts of Cotton–Plant Parts", *Journal of Economic Entomology*, vol. 56, No. 4, pp. 449–454 (Aug. 1963).

H. G. Schabel, "Oral Infection of Hylobius Pales by *Metarrhizium anisopliae*", *Journal of Invertebrate Pathology*, vol. 27, No. 3, pp. 377–383 (May 1976).

(List continued on next page.)

OTHER PUBLICATIONS

Microbial Control of Pests and Plant Diseases, 1970–1980, published by Academic Press, edited by H. D. Burges, pp. 465–482 (Chapter 24: Pest Control by the Fungi: Beauveria and Metarrhizium, by P. Ferron) ©1981.

Z. Feng et al., "Age–Specific Dose–Mortality Effects of *Beauveria bassiana* (Deuteromycotina: Hyphomycetes) on the European Corn Borer, *Ostrinia nubilalis* (Lepidoptera: Pyralidae)", *Journal of Invertebrate Pathology*, vol. 46, No. 3, pp. 259–264 (Nov. 1985).

*Cotton Insect Management with Special Reference to the Boll Weevil*, Edited by R. L. Ridgway et al., U.S.-D.A.-A.R.S., Agricultural Handbook No. 589, Chapter 8: Pheromones for Survey, Detection & Control (Nov. 1983).

KONSUME TM Insect Feeding Stimulant brochure (Jul. 1989), manufactured by Fermone Corporation, Inc., Phoenix, Arizona.

Ford's Baits and Rodenticides brochure (©1990) manufactured by Ford's Chemical Inc., Pasadena, Texas.

J. E. Wright et al., "Laboratory Evaluation of *Beauveria bassiana* as an Entomopathogen Against the Boll Weevil, 1988", *Insecticide and Acaricide Tests*, vol. 14, p. 258 (1989).

W. L. Parrott et al., "Feeding Response of the Boll Weevil (Coleoptera: Curculionidae) to Ester Extracts of Host Plants", Journal of Economic Entomology, vol. 82, No. 2, pp. 449–453 (Apr. 1989).

Chem. Abstract 72(17) 89237q, V. V. Sukhov, "Biological Method for Combatting the Colorado potato bug, *Leptinotarsa decemlineata*" (1970).

Chem. Abstract vol. 73 (1970) 13464m, I. S. Velitskaya, "Use of the preparation bouverin to combat the European corn borer."

CA vol. 100 (1984) 116441g, T. E. Anderson et al., "Compatibility of *Beauveria bassiana* isolates with insecticide formulations used in Colorado potato beetle (Coleoptera: Chrysomelidae) control."

CA vol. 70 (1969) 46398j, L. I. Brikman et al., "Virulence of entomopathogenic spore–forming microorganisms in relation to the red house ant, *Monomorium pharaonis.*"

CA vol. 86 (1977) 84761k, B. Schaeffenberg et al., German Offen. 2,617,892 (Dec. 9, 1976).

K. H. Veen, "Recherches sur la maladie, due a *Metarrhizium anisopliae* chez le criquet perlerin (with English Summary)," Meded. Landbouwhogeschool Wageningen, Nederland vol.68–5, pp. 1–77 (English Summary pp. 68–71 (1968).

D. D. Hardee et al., "Male Boll Weevils are More Attrative than Cotton Plants to Boll Weevils," Journal of Economic Entomology, vol. 62, No. 1, pp. 165–169 (Feb. 1969).

BIOPESTICIDE COMPOSITION AND PROCESS FOR CONTROLLING INSECT PESTS

This application is a continuation of application Ser. No. 07/892,488 filed Jun. 3, 1992 which is a continuation of application Ser. No. 07/638,489, filed Jan. 9, 1991, now abandoned.

FIELD OF THE INVENTION

This invention relates, in general, to insecticides for controlling insect pests and methods for using such compositions. In one aspect, this invention relates to a biopesticide composition for controlling insect pests, wherein the composition comprises an entomopathogenic fungus having virulence against the insect pest(s), an arrestant and feeding stimulant for the insect pest(s), and, optionally, a pheromone for the insect pest(s). In a further aspect, this invention is directed to the use of such compositions. In another aspect, this invention relates to an isolate of *Beauveria bassiana* which, when in its pure form, has virulence against boll weevils, sweet potato whiteflies and cotton fleahoppers characteristic of *Beauveria bassiana* culture deposit ATCC-74040 (ARSEF 3097).

BACKGROUND OF THE INVENTION

The cotton boll weevil is easily one of the most notorious agricultural pests in the world. It occurs in all principal cotton-growing areas of Central and South America and the United States except parts of California. Wherever it is present, it is the key pest in cotton. The injury is caused by adults and the larvae or grubs. The adult weevils chew into or puncture the squares and bolls, and with their long slender bills, feed on the inner tissues. The eggs are laid in these holes, and the hatching grubs bore into the boll or square, causing the squares to drop off or wither and dry on the plant. This feeding either results in direct destruction of the flower or a reduction of fiber content in the boll. Losses can be so great as to be limiting. In 1982, damage to cotton in the United States was estimated at $429 million dollars. This figure has and is expected to continue to increase.

Chemical insecticides and cultural eontrois are currently employed in the control of boll weevil. These have associated problems and are not completely effective. There is a definite need for alternative materials that can be used in a complementary fashion with existing controls and to replace control agents that may lose efficacy due to resistance or other factors.

Management strategies for boll weevil control seek to attack the insect at the weakest point in its life cycle. Thus, early season adult control is based on insecticide treatment at pinhead square formation to kill overwintering adults prior to their damaging the current crop and beginning reproduction. Because insecticides kill benefieials and pests alike, the predator-prey balance is broken. Surviving insect pests proliferate due to the decreased populations of beneficial predatory insects, and additional insecticide applications become necessary for control of later pests, particularly the bollworm complex, Heliothis spp. Thus, removal of the early season boll weevil is tantamount for production of a viable lint crop. With increased emphasis on protection of the environment, reduction in the use of pesticides, and with increased urbanization and awareness, the need for biopestieides and insect management strategies is acute, and it should become an important factor in sustainable agricultural concepts now being rigorously supported by state and federal institutions. One of the most successful materials, *Bacillus thuringiensis*, has been tested extensively against a boll weevil but remains ineffective.

The sweet potato whitefly *Bemisia tabaei* (Gennadius) has appeared on poinsettias in California, Florida, Georgia and North Carolina. During 1981, the sweet potato whitefly was responsible for crop and market losses of 100 million dollars in cotton, eueurbits and lettuce in California and Arizona. The whitefly is increasingly a problem in Florida where, in 1986, this whitefly caused approximately 2 million dollars of damage to Florida's 8–10 million dollar poinsettia crop.

The sweet potato whitefly is also a pest of international importance, having been found on host plants throughout the mideast Caribbean and Central America. This insect is now known to feed on more than 500 different plants, many of which are of importance in the Caribbean and Florida. For example, cassava, sweet potato, squash, tomato, beans, lettuce, cotton, pepper, carrot, cucumber, eggplant, and water melon are all known hosts. This species of whitefly severely impacts infested plants by its feeding, production of honeydew with resultant growth of sooty mold, and transmission of plant pathogens. Most extensive losses to this pest have been through direct feeding damage and indirect damage through transmission of plant diseases.

Whitefly-borne diseases are of major importance in tropical and subtropical agriculture. More than 70 diseases caused by viruses and microorganisms are known to be transmitted by whiteflies, with most of them being transmitted by the sweet potato whitefly. In Puerto Rico, this whitefly is a vector of at least seven diseases. One of these diseases is the bean golden mosaic virus, a disease affecting many legumes.

The sweet potato whitefly has proven to be very difficult to control with conventional pesticide applications. Many factors contribute to the lack of control obtained with pesticides. The most important factor is that this whitefly has demonstrated a broad spectrum of resistance to chlorinated hydrocarbons, organophosphorus, carbamate, and synthetic pyrethroid insecticides. Very few commercially available pesticides are effective against whiteflies, and those which do work are only effective if care is taken to make a very thorough application of the insecticide several times a week. The sweet potato whitefly spends most of its life on the undersides of leaves, therefore, growers must adjust their management practice to permit increased pesticide coverage there. The spacing of the plants must be such that the chemical spray can penetrate the canopy and reach all surfaces of the plants.

In addition to being largely ineffective, and difficult and costly to apply, chemical control of these pests has other significant drawbacks. For example, the use of chemical pesticides presents the further disadvantages of polluting the environment, creating potential health hazards to agricultural workers and to consumers, development of resistance to chemicals in target pest species, detrimental effect of these chemicals on non-target species resulting in secondary pest outbreaks, and phytotoxic reaction by treated plants.

Because of the problems associated with the use of chemical pesticides, safer and more effective methods of control for insect pests are clearly needed. Although biological control agents are actively being sought after, to date no biological control agent has been commercially successful for the control of the boll weevil and the sweet potato whitefly.

Biological control agents have been tried; however, availability, limited host range, cost and reliability have reduced the potential for implementing the use of these biological control agents. The development of a broad spectrum of pesticides would reduce the need for many of the petrochemically based pesticides. By using fungi to control insect pests, the potential for resistance development is minimized, which, in turn, will stabilize many of the pest management programs.

In many instances, fungi used to control insect pests have not had the effectiveness required for commercial use. Therefore, there also exists a need for enhancing the effectiveness of such entomopathogenic fungi.

SUMMARY OF THE INVENTION

Accordingly, there is provided a biopesticide composition for controlling targeted insect pests, for example, the boll weevil, cotton fleahopper and the sweet potato whitefly. The biopesticide composition comprises an entomopathogenic fungus having virulence against the targeted insect pest(s), an arrestant and feeding stimulant, and, optionally, a pheromone. The entomopathogenie fungus may be a *Beauveria bassiana*, preferably *Beauveria bassiana* culture deposit ATCC-74040 (ARSEF 3097), and routants thereof which substantially retain the virulence of the parent strain against boll weevils, sweet potato whiteflies and cotton fleahoppers. The fungus may also be *Paecilomyces fumosoroseus*, designated Apopka, culture deposit ATCC 20874, and mutants thereof which substantially retain the virulence of the parent strain against whiteflies.

The arrestant and feeding stimulant is preferably one derived from cotton-plant parts and square components, preferably from the cottonseed and/or the water extract of the calyx and androecium parts of the cotton plant.

The pheromone is preferably a sex and/or aggregating attractant specific to the insect pest(s) of interest.

DETAILED DESCRIPTION OF THE INVENTION

A biologically pure culture of a novel isolate of *Beauveria bassiana* of the subject invention has been deposited in the American Type Culture Collection (ATCC), 12301 Parklawn Drive, Rockville, Md. 20852 and arranged accession No. ATCC 74040. This same novel isolate was also accessioned into the USDA-ARS Collection of Entomopathogenic Fungal Cultures as ARSEF 3097 at which time the culture was confirmed to be a *Beauveria bassiana* (Balsamo) Vuillemin. The USDA-ARS accession record for this strain has been marked for restricted distribution, whereby the USDA-ARS will not release this fungus for use by any laboratory without permission of the depositor.

| Culture | Accession No. | Deposit Date |
|---|---|---|
| *Beauveria bassiana* | ATCC-74040 | March 11, 1991 |

As noted above, the USDA-ARS deposit is restricted and will not released without permission of the depositor. The subject culture is deposited under conditions that assure that access to the culture will be available during the pendency of the patent application to one determined by the Commissioner of Patents and Trademarks to be entitled thereto under 37 C.F.R. § 1.14 and 35 U.S.C. § 1.22. The ATCC deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Furthermore, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, or in any case, for a period of at least thirty (30) years after the date of deposit or for the enforceable life of any patent which may issue disclosing the culture. The depositor acknowledges the duty to furnish a sample when requested, due to the condition of the deposit. All restrictions on the availability to the public of the subject culture deposit will be irrevocably removed upon the granting of a patent disclosing it.

The entomopathogenic fungus *Beauveria bassiana* is an imperfect fungus (Fungi Imperfecti) and the subdivision Deuteromycotina. The genus *Beauveria Vuill* is within the Class Deuteromycetes and is distinguished from other genera by having conidia that are borne singly, not catenulate and having the fertile portion of the conidiophore zig-zag in shape and drawn out at the tip. The species *Beauveria bassiana* has spherical not ellipsoid conidia measuring 2–3 micrometers by 2–2.5 micrometers and with conidiophores forming dense bunches. The novel isolate of *Beauveria bassiana* is the first known fungus of this species which is highly virulent to boll weevils, sweet potato whiteflies and cotton fleahoppers.

Like most entomogenous fungi, *Beauveria bassiana* initiates infection by a germinating spore (conidium) attaching to and subsequently penetrating the cuticle of the insect host. The claimed *Beauveria bassiana* attaches very securely to the cuticle of the targeted insect pest and is typically not removed by the grooming activities thereof. This may account somewhat for the high virulence of the fungus. As the fungus penetrates the target pest cuticle, the invasive hyphae begin to enter the host tissues and ramify through the hemocoel. Hyphal bodies or segments of the hyphae distribute throughout the hemocoel, filling the dying insect with mycelium. Emergence hyphae grow out through the insect's integument and produce spores on the external surface of the host. These spores, or conidia, are dispersed and capable of infecting new host insect pests.

The fungus works rapidly; a remarkable 80 to 90 percent kill of the adult boll weevil occurs within 3 to 10 days of application. Significantly, more than 90 percent of the kill occurred within one week of application. Spore concentrations of from about $2 \times 10^8$ to about $2 \times 10^{14}$ spores per milliliter of carrier can be used. Spore application rates of from about $1 \times 10^{12}$ to about $10 \times 10^{12}$ per acre can be used, preferably about $4.5 \times 10^{12}$ to about $6.25 \times 10^{12}$ conidia per acre.

This particular *Beauveria bassiana* may be cultured and mass produced by methods used to culture *Beauveria* spp. See for example, U.S. Pat. No. 4,925,663; *Micobial Control of Pests and Plant Diseases* 1970–1980, published by Academic Press, pages 471–473 (1981; edited by H. D. Burges); and Feng et al., *J. Invertebrate*

*Pathology*, Vol. 46, no. 3, November 1985, page 260, the disclosures of which are hereby incorporated by reference.

In another aspect of the present invention, a biopesticide composition for controlling targeted insect pests is provided. The biopesticide composition comprises an entomopathogenic fungus having virulence against the targeted insect pests, an arrestant and feeding stimulant, and, optionally, a pheromone. In this manner, contact with the fungus is enhanced by the attractive properties of the arrestant and feeding stimulant and, optionally, in conjunction with a sex or aggregating pheromone. As noted above, in the discussion of the *Beauveria bassiana,* the mode of infection of fungi is generally by cuticular penetration by the germ tube of the fungal conidia and may also occur through the respiratory or alimentary tract (such as mouth parts). Additionally, ingestive fungal spores voided in the feces may provide another source of contact with the cuticle of the targeted insect pest. Death in the host may occur either by release of fungal toxins or by tissue destruction. The fungal growth range is between 40° and 95° F. in a wide range of humidity with high humidity necessary to germinate spores and to increase spore production on the crops or plants being protected by the biopesticide.

Entomopathogenic fungi which may be used in the biopesticide composition of the present invention include but are not limited to:

Beauveria spp.
Metarhizium spp.
Paecilomyeus spp.
Akanthomyees spp.
Gibellula spp.
Pseudogibellula spp.
Hymenostilbe spp.
Spicaria spp.
Nomuraea spp.
Cephalosporium spp.
Sporotriehum spp.
Torubiella spp.
Cordyceps spp.
Aspergillus spp.
Entomopathora spp.
Paeeilomyees spp.

The following fungi are specific examples which are suitable in the biopesticide composition of the present invention. *Beauveria bassiana* No. RS-252 available from Abbott Laboratories, Chicago, Ill., which is useful against cotton boll weevils.

*Beauveria bassiana* culture deposit ATCC-74040 (also deposited with the USDA-ARS having accession No. ARSEF-3097) useful in the control of cotton boll weevil, sweet potato whitefly, and cotton fleahopper.

*Paecilomyees fumosoroseus,* designated Apopka, culture deposit ATCC-20874 (See U.S. Pat. No. 4,942,030, the disclosure of which is incorporated herein by reference) useful in the control of the sweet potato whitefly, onion thrips, beet army worm, Colorado potato beetle, gypsy moth, two-spotted spider mite, flower thrips, Citrus mealybug, and Solanum mealybug.

*Beauveria bassiana* No. 447 culture deposit ATCC-20872 (See U.S. Pat. No. 4,925,663, the disclosure of which is incorporated herein by reference) useful in the control of imported fire ants.

The arrestant and feeding stimulant may be broad based to a variety of insect pests or tailored to a specific insect pests. In regards to insect pests of cotton, the arrestant and feeding stimulant is preferably one derived from cotton plant parts and square components, preferably from cottonseed and/or the water extract of the calyx and androecium parts of the cotton plant. Examples of such insect pests include the boll weevil, sweet potato whitefly, and the cotton fleahopper.

A broad based feeding stimulant suitable for use in the biopesticide composition of the present invention is a combination of protein, carbohydrates and lipid oil which may be formulated as an aqueous suspension, wettable powder, dry flowable water, dispersible granule, granular bait or dust. These three ingredients may be present at concentrations of 10 to 100 percent by weight of the feeding stimulant. The ratio of the protein, carbohydrate and lipid oil components is preferably in the range of about 1:1:0.2 to about 1:2:0.03 with a particularly preferred ratio being 42.5:55:2.5. The protein sources are preferably high protein sources having about 40 to about 70 percent by weight protein. Furthermore, vegetable protein is preferred over animal protein. Examples of vegetable protein is the protein included in soybeans, cotton seed and the like. Particularly preferred is cottonseed flour which has been defatted (preferably less than 4% by weight fat), low gossypol (preferably less than 0.05% by weight), high in protein (preferably from about 55 to about 60% by weight), finely milled (preferably 100% of the cottonseed flour is less than 75 micron in size) and contains carbohydrates at about 25 to 30%, preferably about 28% by weight. Additional carbohydrate sources may be included such as cane or beet sugar. Likewise, additional lipid oil sources such as refined cottonseed oil, corn oil, soybean oil, and the like, preferably cottonseed oil, may be added.

Fire ants may vary their preferences from day to day by variously seeking sugars, starches, proteins and oils for their diet. Therefore, an arrestant and feeding stimulant containing these four items would be a universal feeding stimulant satisfying the varying dietary demands of the fire ants.

The arrestant and feeding stimulant may have additional components comprising the various types of aids known to those skilled in the art which include but are not limited to diluents such as water, clays and the like, formulation aids such as emulsifiers, application aids such as dispersants, wetting agents, spreader-stickers, and the like, and UV protectors.

The arrestant and feeding stimulant is preferably used at rate per acre ranging from 0.25 to about 10 lbs. based on the weight of the protein, carbohydrate and lipid oil sources. Preferably, the range is from about 0.5 to about 2 lbs. per acre based on the weight of the protein, carbohydrates and lipid oil sources.

The pheromone in the biopesticide composition is optional in that the arrestant and feeding stimulant in and of itself is a food lure that acts as an attractant to the targeted insect pests.

In general, pheromones or attractants may be classified as sex, food, or oviposition lures. Additional classifications or subclassifications include trail pheromones, aggregating and other pheromones. Broadly defined, a sex pheromone is an odor released by one member of the species which attracts the opposite member for the purpose of mating. The presence of sex pheromones has been demonstrated in most orders of insects and they can be produced by the male or female of the species. In many eases, it is the female which produces the attractant. A large number of pheromones that are useful in the biopesticide compositions of the present invention may be naturally or synthetically obtained. Pheromones and attractants are well known by those skilled in the art. Examples of such pheromones and attractants are disclosed in U.S. Pat. Nos. 4,908,977 and 3,895,078, the disclosures of which are incorporated herein by reference. When included, the pheromone may be incorporated in the biopesticide composition of the present invention in a controlled release form.

A preferred pheromone is the sex pheromone of the male boll weevil also known as grandlure which is comprised of four monoterpenoid components which are disclosed in U.S. Pat. No. 3,895,078. The components are (I) (+)-cis-2-isopropenyl-1-methylcyclobutaneethanol; (II) (Z)-3,3-di-methyl-delta$^{1,beta}$-cyclohexaneethanol; (III) (Z)-3,3-dimethyl-delta$^{1,alpha}$-cyclohexaneacetaldehyde; and (IV) (E)-3,3-dimethyl-delta$^{1,alpha}$-cyclohexaneacetaldehyde. These components are preferably present in the following range: Component I: from about 30 to about 35% by weight, component II: from about 35 to about 40% by weight, component III: from about 13 to about 15%, and IV: from about 13 to about 15% by weight. A particularly preferred ratio is about 30:40:15:15, respectively. The rate of usage of the pheromone is preferably from about 25 to about 1,000 milligrams per acre, more preferably from about 40 to about 400 milligrams per acre.

In regards to boll weevils, the biopesticide composition is preferably applied when the outside ambient temperatures range from about 10° C. to about 40° C. which is conducive to adult boll weevil flight. Applications are preferably made on a multiple basis at five (5) day intervals until the population of boll weevils is below an economic threshold. Application of the fungus and/or the biopesticide composition may be accomplished using standard operating equipment used in the agricultural industry, for example, a tractor or airplane equipped with booms and nozzles for spraying the composition in a liquid carrier.

The following examples are for illustrative purposes only and are not meant to limit the claimed invention in any manner.

EXAMPLES

EXAMPLE No. 1

Feeding Substrate Evaluations

The boll weevil primarily feeds and reproduces on cotton although other plants have been identified as alternative hosts. In the present example, commercially available materials containing cotton plant derive products that were evaluated as potential feeding substrates for the adult boll weevil. The products evaluated were: Proflo which is a cottonseed derived protein from Traders Protein, Memphis, Tex.; Konsume TM from Fermone Corporation, Inc., Phoenix, Ariz.; and cottonseed oil (twice refined) from Valley Co-op Oil Mill, Harlingen, Tex. Konsume TM feeding stimulant contains a mixture of cottonseed flour, disaccharide, vegetable lipid oil, alcohol alkoxylate (emulsifier), and polysaccharide (thickener).

Laboratory evaluations in this example and the following example were performed with boll weevils obtained from Robert T. Gast Rearing Laboratory at Mississippi State, Miss., and reared by the method of Robinson and Wright disclosed in *Advances and Challenges and Insect Rearing*, pages 188–192, U.S. Department of Agriculture, Washington, D.C. (1984; editors E. G. King and N. C. Leppa).

Solutions of each of the potential feeding substrates in water were prepared at concentrations of 0, 10, 30, 50, 80 and 100 percent or each of the substrate materials. Five squares each about 400 to 600 milligrams were immersed into each solution and placed in 100 millimeter glass petri dishes with ten boll weevils. The weevils were 3–5 days of age, of mixed sexes and had not received food nor water for 24 hours. The number of adults observed feeding at time intervals of 30 and 60 minutes and the number of feeding punctures in the squares at 24 hours were the criteria used to differentiate between the substrates (10 replications). Further the evaluations were made by placement of the respective materials on dental cotton rolls to determine if adults would feed on the substrates if placed on an abstract material.

As noted in Table 1, adults fed readily on each of the three substrates evaluated. At the higher concentrations (30 percent plus) of all materials evaluated, fewer adults were observed to feed as the substrates were oily or sticky and apparently the physical condition acted as a deterrent. Some mortality was observed at 24 hour post-feeding for the cottonseed oil and Prorio substrates whereas none were observed with Konsume TM substrate. The number of feeding punctures (Table 1) provided data that supported the number of adults observed to feed on the substrate treated squares. The Konsume TM substrate, in both cases, was the choice as determined statistically with more adults observed to feed as well as more feeding punctures in the squares.

The next evaluation was to determine if adults would feed on substrates if placed on an inert material other than the fresh cotton squares. Cotton dental wicks were immersed in 10 percent solutions of cottonseed oil, Proflo and Konsume TM, and the data in Table 2 show that the adults feeding on the substrates were not deterred by the placement of the substrates on the cotton dental rolls. No significant differences were observed among the three feeding substrates in feeding activity. As noted in Table 3, a comparison with treated squares and dental cotton roll reveal no significant differences when a choice was available to the adults.

TABLE 1

Substrate evaluation for a biopesticide as determined by attractancy and feeding behavior of the boll weevil.
Feeding Activity of Adults

| Substrate | x ± se observed feeding[A] | x ± se punctures/squares[A] |
|---|---|---|
| Cottonseed oil | 2.11 ± 0.19 a | 18.95 ± 2.56 a |
| Konsume TM | 3.28 ± 0.21 b | 29.52 ± 3.08 b |
| Proflo | 2.89 ± 0.21 a | 21.33 ± 3.06 a |

[A]Means followed by the same letter in each test are not significantly different, t-test analysis (P < 0.05).

TABLE 2

Substrate evaluation for a biopesticide as determined by attractancy and feeding behavior of adult boll weevil when the Substrate was placed on an inert material.
Feeding activity of adults

| Substrate | x ± se observed feeding[A] |
|---|---|
| Cottonseed oil | 6.25 ± 4.25 a |
| Konsume TM | 5.5 ± 4.5 a |
| Proflo | 8.0 ± 2.91 a |

[A]Means followed by the same letter are not significantly different, t-test analysis (P < 0.05).

TABLE 3

Feeding behavior of adult boll weevils when Substrate was placed on squares or cotton wicks: choice evaluation.

| Substrate on | Feeding activity of adults x ± se observed feeding[4] |
| --- | --- |
| Squares | 3.11 ± 0.27 a |
| Cotton filters | 2.8 ± 0.24 a |

[4]Means followed by the same letter are not significantly different, t-test analysis (P < 0.05).

EXAMPLE 2

Laboratory Evaluation of an Embodiment of the Biopesticide

In this example, the combination of boll weevil pheromone (0.1 milligrams per milliliter), feeding substrates (10%), and entomopathogenic fungus (1%) on dental rolls was placed on top of screen cages holding adult boll weevils. The fungus was *Beauveria bassiana* in the form of a technical powder obtained from Abbott Laboratories, North Chicago, Ill.

Adult boll weevils were observed to readily feed on the combination and after five days more than 90 percent were dead. Fungus growth was externally apparent. The pheromone was a grandlure preparation. The dead adults were dissected to determine the presence of *Beauveria bassiana*.

EXAMPLE 3

Preliminary Field Evaluation of Biopesticide

In this example, a preliminary field evaluation of the biopesticide involved the placement of ten milliliters of the solutions used in the previous example on sanitary napkin pads located on stands two meters high at the edges of a cotton field in the Fall of 1987. Numbers of adults that responded to the biopesticide were visually counted after two hours.

No difference in attractancy or feeding by adults was observed among the three feeding substrates. It was difficult to quantify this type of evaluation other than to record a number of adults at a given time to indicate that adults would or would not respond to the biopesticide. The observations provided data that indicated a positive response.

EXAMPLE 4

Overwintered Adults in Early Season Cotton

In this example, the biopesticide was evaluated against over-wintered boll weevil adults on cotton. The evaluation was initiated in the Spring months on a 14-acre cotton block in North East Hidalgo County. The field was divided into two-seven acre sections: one for the boll weevil biopesticide and one for conventional insecticide treatments for early season boll weevils. Each section was further divided into one acre subsections in each treatment. Pheromone traps that contained no pheromone were placed five per subsection (one acre) and monitored prior to planting of cotton and throughout the test. The objective of this evaluation was to determine if adults were induced to come into the cotton early in response to the boll weevil biopesticide and to determine if the fungus *Beauveria bassiana* (Abbott Labs.) would be an effective pathogen.

At the six leaf stage of growth in the cotton, applications of the boll weevil bioinsecticide were initiated. The biopesticide contained about 681 grams of conidia (one gram had about $1 \times 10^{10}$ spores as corrected spore viability); about 8.5 liters of Konsume TM; about 2.0 grams pheromone (grandlure preparation) in a total volume of about 170 liters. A highboy sprayer with 8,002 nozzles, six rowband at about 40 centimeters high was used to apply about 19.4 liters per hectare. Adult boll weevils were placed in individual screened cages on the ground prior to the application of the bispesticide and removed immediately thereafter to the laboratory for determination of pathogenicity of *Beauveria bassiana* (25 adults per container with one container per acre treated subsection). After application, boll weevil adults (5 per plant on 5 plants in subsection plots) were retained on the plants by 20 centimeter plexiglass tubing for 24 hours and then removed to the laboratory for fungal evaluation in the last two applications. Agar plates containing Sabouraud Dextrose Agar and Yeast Extract [about 40 gm. dextrose, about 10 gms Neopeptone (Difco), about 15 gm. agar and about 10 gm. yeast extract per 1000 mi. water] medium (See Fenge et al., infra.) (14 in treated and 14 in non-treated subsample plots) were returned to the laboratory and held at 95% relative humidity and 29° C. for determination of fungal growth.

Adults were removed from the non-baited pheromone traps from the treated and non-treated plots and held in the laboratory to determine the presence of the fungus. Five traps per acre gave a total of 70 pheromone traps within the field.

As the cotton matures and few feeding and ovipositional sites are available near the termination of the cotton production season, adult boll weevils begin to search for additional food and over-wintering habitat. The objective of the testing of the boll weevil biopesticide at this time would be to attract those dispersing adults to the biopesticide, on non-cotton habitat as well as regrowth cotton, and determining pathogenicity of the fungus. The regrowth cotton occurs when the crop is shreaded and not immediately plowed. The regrowth gives the adult boll weevils feeding sites and probably increases a number of the adults that survived the winter. Plowdown or the destruction of the cotton stocks has been a recommended and accepted agricultural method for reduction of overwintered adult population since the early 1900's.

The results of the biopesticide applications on adult boll weevils when applied to early season cotton are given in Table 4. Adults that were placed in the screened cages at the time of application will return to the laboratory with the results that 78.02%±6.12% adults (number of adults=641) were killed by the fungus *Beauveria bassiana* (Abbott Labs.). It is noted that these cages were placed at ground surface between the cotton plants and therefore the exposure to the *Beauveria bassiana* in the biopesticide would have been less than total. Adult boll weevils that were caged on plants after application of the bioinsecticide had a mortality factor of 92.54%±6.5% (number of boll weevils=139) due to *Beauveria bassiana* (see Table 4). Adult boll weevils captured in the non-baited pheromone traps averaged 11% mortality due to *Beauveria bassiana* (number of boll weevils=100).

TABLE 4

Results of biopesticide applications on adult boll weevils when applied to early season cotton.

| Method of Exposure | Pathogenic Activity of Beauveria x % ± se mortality |
| --- | --- |
| Screen cages | 78.02 ± 6.12 |

TABLE 4-continued

Results of biopesticide applications on adult boll
weevils when applied to early season cotton.
Pathogenic Activity of Beauveria

| Method of Exposure | x % ± se mortality |
| --- | --- |
| Caged plants | 92.54 ± 6.5 |

EXAMPLE 5

Non-Cotton Habitat Test

In this example, an area of rangeland grasses was identified as a non-cotton/boll weevil habitat and used to evaluate the attractancy of the boll weevil biopesticide during the period of adult dispersal. Plot size was about 0.25 acre and three were treated with the boll weevil biopesticide and three served as controls. The plots were three miles apart. Pheromone traps (5 unbaited) were placed equal distantly within the plots for evaluation of adults that were attracted by the bioinseetieide. Sweep nets were used to capture adults within the grass. The adults were returned and challenged in the laboratory for the presence of the *Beauveria bassiana* (Abbott Labs.) which would indicate that contact had been made with the bioinseetieide, whether per os or externally. The boll weevil biopesticide formulation used was about 3.78 liters of Konsume TM feeding substrate, about 1.89 liters of Nufilm 17, about 40 grams of calco oil red, about 400 milligrams of pheromone, about 100 grams of *Beauveria bassiana* and about 151.4 liters of water. Nufilm 17 is about 96% di-1-p-menthene, available from Miller Chemical and Fertilizer Corp., Hanover, Pa. The Nufilm 17 acts as a sticker spreader, extender and antitransparent. The *Beauvecia bassiana* is of the strain identified as RS-252 available from Abbott Laboratories, Chicago, Ill. Four applications at 4-day intervals were applied.

The results of the application of the boll weevil biopesticide to rangeland grass plots indicated that a significant number of adult boll weevils were attracted to the treated plots when compared to nontreated controls (P=<0.05, number=92). Of those adults captured either by non-baited pheromone traps or by sweep nets, about were found to be infected by *Beauveria bassiena*.

EXAMPLE 6

Regrowth Cotton Test

In this example, cotton was shreaded and allowed to regrow on eight (8) 1-acre sites to provide an area in which to evaluate the boll weevil biopesticide. Three applications at five-day intervals were made on the regrowth cotton and adult boll weevils were hand collected by visible inspections of the plant or by the use of sweep nets. Four plots, about 1 acre each, were treated and four were left untreated. Unbaited pheromone traps, five per acre, also were placed on each plot. The boll weevil biopesticide and application was the same as used in Example 5 in the non-cotton habitat treatments. Adults removed from the plots were returned to laboratory and challenged for fungal activity.

The regrowth application of the bioinsecticide to the regrowth cotton plots resulted in about 60.1% infection with *Beauveria bassiana* in adults captured (number=158) in the treated plots.

EXAMPLE 7

Bait Stations

In this example, bait stations were developed using one gallon plastic milk containers by removing the sides and placing a wire platform in the bottom so that about 300 milliliters of solution could be placed in the bottom and the adult boll weevils could land on the wire and feed. This test was evaluated in a brushy habitat at least 50 miles north of any cotton production. The bait stations, located on top of 2 meter stakes, were about one mile apart and the formulations evaluated were replicated three times with nine evaluations made. Adult boll weevils were removed and counted after an hour interval to determine attractancy. Adult boll weevils were returned to the laboratory (number=10 if available or less) and challenged for mortality. The *Beauveria bassiana* (Abbott Labs.) was present in the solution at a concentration of 1% ($1 \times 10^{10}$ conidia per gram). The feeding substrate, Konsume TM, was diluted 50% with water and three formulations with pheromone (10 milligrams per bait station) were evaluated: an encapsulated pheromone; a formulated lure strip available from Hercon Laboratories, South Plainfield, N.J.; and a grandlure preparation.

As shown in Table 5, the evaluation of different pheromone formulations in the bait station reveals significant differences in the number of adults captured. The grandlure preparation when combined with the feeding substrate and *Beauveria bassiana* attracted significantly more adult boll weevils than the encapsulated pheromone or the lure strip. When the adult boll weevils were challenged for the presence of *Beauveria bassiana*, no significant differences occurred between those captured from the bait stations with the lure strip and the grandlure but there was a significant difference between those caught and these two the encapsulated pheromone/feeding substrate combination, as shown in Table 6.

TABLE 5

Evaluation of pheromone formulations in the
biopesticide placed in bait stations.
Numbers of adults captured in 1 hour

| Formulation 10 mg.[a] | x ± se adults[b] |
| --- | --- |
| Konsume TM ls | 33.29 ± 6.93 a |
| Konsume TM gl | 64.92 ± 19.74 b |
| Konsume TM ec | 0.7 ± 0.24 c |
| Konsume TM (alone) | 0 d |

[a]ls = lure strip gl = grandlure formulation; ec = starch encapsulation; Konsume TM = feeding substrate.
[b]Means followed by the same letter are not significantly different, t-test (P < 0.05).

TABLE 6

Evaluation of pathogenicity of the
biopesticide when placed in bait stations.
Percent of adults infected with Beauveria

| Formulations[a] | x ± se Mortality[b] |
| --- | --- |
| Konsume TM ls | 37.77 ± 6.82 a |
| Konsume TM gl | 51.1 ± 22.64 b |
| Konsume TM ec | 14.7 ± 7.56 c |
| Konsume TM (alone) | 0 d |

[a]ls = lure strip gl = grandlure formulation; ec = starch encapsulation; Konsume TM = feeding substrate.
[b]Means followed by the same letter are not significantly different, t-test (P < 0.05).

EXAMPLE 8

Experimental Field Trials

Experimental field trials were conducted at the Subtropical Agricultural Research Laboratory in the lower Rio Grande Valley where the boll weevil is the major pest of cotton. The field experimental design was a replicated block, five times in the first trial, and three times in the second trial. Each plot was about 1 acre. Cotton cultivar was Gossypium hirsutum L., "DES-119", on Irrigated Sandy Clay Loam Land. Plots in the first field trial were treated with Composition A and plots in the second field trial were treated with Composition B at approximately the 8-leaf stage and then on a weekly schedule thereafter for a total of six applications. Following these applications with the biopesticide, conventional insecticides were then used throughout the remainder of the cotton production season. The application equipment utilized was a John Deere, 6000 Ground Rig Sprayer which delivered about 8 gallons per acre.

The treatments evaluated in the first field trial were Composition A according to the present which utilized a Beauveria bassiana from Abbott Laboratories (strain RS-252) which was compared to control C1 which was the insecticide Bidtin only. Bidrin is (E)-2-dimethylcarbamoyl-1-methylvinyl dimethyl phosphate (CAS: 41-66-2). In the second field trial, the treatments were with Composition B according to the present invention, control C2 and control C3. Composition B utilized the fungus Beauveria bassiana, deposit ATCC-74040 (also accessioned as ASREF-3097). Control C2 utilized the insecticide Guthion only and control C3 utilized the insecticide Guthion in conjunction with the feeding stimulant utilized in Composition B. Guthion is O,O-dimethyl-S-[(4-oxo-1,2,3-benzotriazin-3(4H)-yl) methyl ]phosphoro dithioate (CAS: 86-50-0).

The formulations for compositions A and B are shown in Table 7. Other than the particular fungus used, the compositions were otherwise the same. These were added to water to make a total volume of about 8 gallons.

TABLE 7

| Fungus: | |
|---|---|
| Composition A | Beauveria bassiana (Abbott Labs.)[a] |
| Composition B | Beauveria bassiana (ATCC-74040)[b] |
| Arrestant/Feeding Stimulant: | |
| Formulation:[c] | 1. cottonseed flour[d] |
| | 2. cottonseed oil |
| | 3. sugar (disaccharide) |
| | 4. emulsifier[e] |
| | 5. thickener[f] |
| | 6. water and other inerts[i] |
| Pheromone: | Grandlure[g] |

TABLE 7-continued

| Aids | Nufilm 17[h] |
|---|---|

[a] suspended in water with 0.05% Tween X-100, a wetting agent; total volume of the suspension was about 270 milliliters.
[b] suspended in oil; total volume of the suspension was about 270 milliliters; fungus also accessiones as ARSEF 3097 by the USDA-ARS.
[c] Components 1-5 of the formulation compose about 34% by weight of the formulation with component 6 composing the remainder. The protein, carbohydrate and lipid oil content of components 1-3 combined is in a weight ratio of about 42.5:55:2.5 of protein to carbohydrate to lipid oil. Total volume of the formulation was about 1 quart.
[d] Defatted (<4% fat), low gossypol (<0.05%), high protein (55–60%), finely milled (100% <75 microns) cottonseed flour containing about 28% carbohydrates.
[e] Arnox 2404, an alcohol alkoxylate available from Witco Corp., Houston, Tx.
[f] Xantham gum.
[g] The weight ratio of components I, II, III and IV was about 30:40:15:15 respectively. Total weight of the Grandlure was about 400 mg.
[h] About 1 pint total volume.
[i] The other inerts in the formulation do not add or detract to the arresting and feed stimulating properties of the formulation.

The application rates were Bidrin (one pint per acre), Guthion (about one pint per acre), Beauveria Bassiana from Abbott Laboratories at $4.54 \times 10^{12}$ conidia per acre and in Composition B Beauveria bassiana deposit ATCC-74040, at $6.26 \times 10^{12}$ conidia per acre.

Adult boll weevils in screened petri dishes were placed within the rows at the time of application, then returned to the laboratory and challenged for Beauveria bassiana (25 adults boll weevils per petri dish: five dishes per plot per application). Adult boll weevils were also placed on treated plants enclosed in plexiglass tubes, left for 24 hours, then removed to the laboratory and challenged for Beauveria bassiana. (Five adults per plant: Five plants per plot per application).

Plant density, plant height, and fruit numbers (squares, bolls) clean, damaged, and total were taken at five sites within the plot. At each of these sites, measurements were taken at random for two one-meter row areas at various times during early crop development to determine the impact of early treatments with the biopesticide of the present invention.

Boll weevil pheromone traps (four) baited with 10 milligram lure strips from Hereon Laboratories were located at the corners of the test field. During the four-month period of field trials 1 and 2, 722 and 517 adult boll weevils were captured, respectively. The results for field trials 1 and 2 are shown in Tables 8 and 9, respectively. In each of the two field trials, the biopesticide of the present invention yielded significantly more than the control without treatment (Nontreated) and less than that of the insecticide treatment controls (C1, C2, and C3). The activity of the biopesticide is slower than that of the insecticide controls and as such the differences therebetween were expected. The addition of the feeding stimulant to the insecticide Guthion and the results thereof substantiated the relative attractiveness of the feeding stimulant to adult boll weevils.

The mortality of the boll weevil adult exposed in petri dishes is given in Table 10 and no significant differences were detected between the two field trials in this regard. The pathogenicity of the Beauveria bassiana is not immediate as that of a toxicant such as Guthion or Bidtin; however, the combined effect of contact activity of the fungus and ingestion thereof within the feeding stimulant gives excellent mortality for a biopesticide. The mortality of adult boll weevils caged on plants after treatment is given in Table 11 and is at a similar level when compared to Table 10. Also, activity is present for 72 hours post-treatment in this evaluation method, although declining. (See Table 11).

Plant height characteristics for field trials one and two, that is, plant height, plants for row meter, and fruiting levels are given in Tables 12, 13, 14 and 15. The data indicate no difference is attributable to the treatments are present in any of the measured parameters with the exception of fruit which is given in Table 14 which at the time of measurement the non-treated plots had less than the treated plots which were indicative of the boll weevil activity.

Table 16, status of cotton, provides the data that is reflected in the final yield data for the treatments and shows the effects of the early season treatment using the biopesticide of the present invention as well as that of the insecticide controls on the potential crop. Relative levels of damage can be compared to show the effects of the biopesticide to that of the insecticide.

The change from a wettable powder formulation in Composition A to that of a flowable suspension in Composition B improved considerably the application of the biopesticide. Composition B should also have improved the activity in that cuticles are lipophilie and are more susceptible to the absorption of an oil whereas water-based formulations tend to run off. The conidia of the fungus are hydrophobic and are not easily wetted so that the oil provides a better base for expression of contact activity. An improvement in lint yield was noted from the first field trial to the second field trial.

Statistical analysis of data in the present example was accomplished with an analysis of variance (ANOVA) and Tukeys HSD test (T-test) was used to assign significant differences between individual treatments and the non-treated control. (According to the procedure given in MStat. 1987. Michigan State University). Unless indicated otherwise, $P<0.05$ was the criterion used for determining significant treatment effects.

TABLE 8

| Mean lbs $\pm$ S.D. of lint production per acre, Field Trial 1 | |
|---|---|
| Treatment | Yield $\pm$ S.D.[1] |
| Control C1 | 367.0 $\pm$ 72.0 a |
| Composition A | 216.9 $\pm$ 128.1 b |
| Nontreated | 126.9 $\pm$ 47.9 c |

[1]One way analysis of variance; means separated by Tukeys HSD test (P < 0.05). One acre plots with 5 randomized replications.

TABLE 9

| Mean lbs $\pm$ S.D. of lint production per acre, Field Trial 2. | |
|---|---|
| Treatment | Yield $\pm$ S.D.[1] |
| Control C2 | 431.1 $\pm$ 117.0 a |
| Composition B | 281.0 $\pm$ 107.1 b |
| Control C3 | 482.2 $\pm$ 154.5 c |
| Nontreated | 134.6 $\pm$ 50.5 d |

[1]One way analysis of variance; means separated by Tukeys HSD test (P < 0.05). One acre plots replicated 3 times.

TABLE 10

| Mortality of adults exposed in petri dishes after application | | |
|---|---|---|
| Field Trial | N | % Dead $\pm$ S.D.[1] |
| 1 | 1950 | 83.5 $\pm$ 17.5 a |
| 2 | 2477 | 89.6 $\pm$ 9.3 a |

[1]Means followed by same letter are not significantly different (T-Test, P < 0.05).

It will be apparent from the foregoing that many other variations and modifications being made in the methods and the compositions hereinbefore described by those having experience in this technology, without departing from the concept of the present invention. Accordingly, it should be clearly understood that the methods and compositions referred to herein in the foregoing description are illustrative only and are not intended to have any limitations on the scope of the invention.

TABLE 11

| Mortality of adults caged on individual plants after treatment | | | |
|---|---|---|---|
| Exposure Post-Treatment H | Field Trial | % Dead $\pm$ S.D.[1] | |
| | 1 | 2 | 1989 | 1990 |
| 24 | 510 | 375 | 81.0 $\pm$ 18.9 | 82.6 $\pm$ 15.5 |
| 48 | — | 377 | — | 79.5 $\pm$ 23.6 |
| 72 | — | 288 | — | 73.1 $\pm$ 12.5 |

[1]Means followed by same letter are not significantly different (T-Test, P < 0.05).

TABLE 12

| Plant characteristics, Field Trial 1. | | | |
|---|---|---|---|
| | Plant Ht (cm) $\pm$ S.D. | Plants/ M $\pm$ S.D. | Fruit/ M $\pm$ S.D. |
| Composition A | 34.8 $\pm$ 7.3 a | 19.2 $\pm$ 7.1 a | 118.6 $\pm$ 56.2 a |
| Control C1 | 31.9 $\pm$ 4.7 a | 20.1 $\pm$ 11.1 a | 84.0 $\pm$ 35.1 b |

[1]Means followed by a different letter are significantly different (T-Test P < 0.05).

TABLE 13

| Plant Height (cm) $\pm$ S.D. Field Trial 2. | | | | | | |
|---|---|---|---|---|---|---|
| | Date of Sample | | | | | |
| Treatment | 4/16 | 4/23 | 4/30 | 5/08 | 5/25 | 5/20 |
| Control C3 | 14.0 $\pm$ 2.1 | 11.5 $\pm$ 2.2 | 17.5 $\pm$ 2.0 | 22.8 $\pm$ 3.0 | 41.9 $\pm$ 6.5 | 57.0 $\pm$ 4.0 |
| Control C2 | 9.6 $\pm$ 2.3 | 11.8 $\pm$ 2.3 | 17.9 $\pm$ 3.1 | 22.0 $\pm$ 4.4 | 42.5 $\pm$ 8.0 | 55.5 $\pm$ 8.8 |
| Composition B | 10.4 $\pm$ 1.5 | 11.4 $\pm$ 2.6 | 17.6 $\pm$ 3.2 | 21.09 $\pm$ 4.9 | 35.6 $\pm$ 5.9 | 40.0 $\pm$ 6.9 |
| Nontreated | | | | | | |

TABLE 14

| Fruit per meter row $\pm$ S.D., Field Trial 2. | | |
|---|---|---|
| | Date of Sample | |
| Treatment | 5/8 | 5/25 |
| Control C3 | 2.6 $\pm$ 1.9 | 70.8 $\pm$ 18.5 |
| Control C2 | 2.4 $\pm$ 1.6 | 89.3 $\pm$ 32.5 |
| Composition B | 2.2 $\pm$ 1.6 | 78.2 $\pm$ 26.9 |
| Nontreated | | 51.6 $\pm$ 9.9 |

TABLE 15

| Plants per meter row $\pm$ S.D., Field Trial 2. | | | | | |
|---|---|---|---|---|---|
| | Date of Sample | | | | |
| Treatment | 4/16 | 4/23 | 4/30 | 5/08 | 5/25 |
| Control C3 | 14.1 $\pm$ 3.9 | 12.6 $\pm$ 3.9 | 13.1 $\pm$ 2.7 | 16.1 $\pm$ 3.3 | 13.4 $\pm$ 3.6 |
| Control C2 | 12.3 $\pm$ 4.1 | 12.1 $\pm$ 3.4 | 10.8 $\pm$ 3.0 | 15.7 $\pm$ 5.0 | 13.9 $\pm$ 6.7 |
| Composition B | 13.6 $\pm$ 4.6 | 11.7 $\pm$ 3.9 | 12.9 $\pm$ 2.9 | 14.3 $\pm$ 3.2 | 13.3 $\pm$ 2.5 |
| Nontreated | | | | | 15.4 $\pm$ 3.1 |

TABLE 16

| Status of cotton, Field Trial 2[4]. | | | |
|---|---|---|---|
| | Treatment | | |
| | Control C2 | Control C3 | Composit. B | Nontreated |
| Square/M | | | | |
| Clean | 29.6 $\pm$ 27.0 | 26.1 $\pm$ 15.8 | 27.4 $\pm$ 24.6 | 0.8 $\pm$ 1.7 |
| Damaged | 11.8 $\pm$ 11.8 | 19.4 $\pm$ 12.8 | 19.4 $\pm$ 17.7 | 1.3 $\pm$ 2.9 |
| Total | 41.5 $\pm$ 34.1 | 41.9 $\pm$ 16.4 | 46.8 $\pm$ 38.0 | 2.1 $\pm$ 4.3 |

TABLE 16-continued

| | Status of cotton, Field Trial 2[A]. | | | |
|---|---|---|---|---|
| | Treatment | | | |
| | Control C2 | Control C3 | Composit. B | Nontreated |
| Bolls/M | | | | |
| Clean | 38.8 ± 18.6 | 34.3 ± 12.8 | 20.2 ± 11.1 | 5.1 ± 4.5 |
| Damaged | 5.8 ± 5.3 | 9.1 ± 8.3 | 8.0 ± 5.8 | 17.5 ± 6.8 |
| Total | 42.6 ± 18.0 | 41.9 ± 16.5 | 28.2 ± 12.9 | 22.6 ± 9.5 |
| Fruit/M | | | | |
| Damaged | 17.6 ± 12.1 | 27.8 ± 16.9 | 27.5 ± 16.8 | 18.8 ± 7.9 |
| Total | 84.5 ± 32.5 | 87.2 ± 26.7 | 74.9 ± 37.4 | 24.6 ± 10.7 |
| Plants/M | 11.7 ± 3.8 | 12.1 ± 3.9 | 11.7 ± 3.3 | 15.7 ± 4.2 |

[A]M = meter row.

EXAMPLE 9

Bioassays of *Beauveria Bassiana,* Deposit ATCC-74040 (ASREF-3097)

In this example, the cotton fleahopper, *Psuedatomoscellis seriatus,* and sweet potato whitefly, *Bemisia tabaei* nymphs and adults were dipped in solutions of the biopesticide Composition B (having about $1 \times 10^{10}$ conidia per milliliter) and observed for mortality due to pathogenicity of the fungus *Beauveria bassiana,* deposit ATCC-74040 (ARSEF-3097).

These laboratory bioassays against the cotton fleahopper and the sweet potato whitefly suggest that both are receptive to the pathogenicity of this particular strain of *Beauveria bassiana.*

What is claimed is:

1. A biologically pure culture of *Beauveria bassiana* having the identifying characteristics of *Beauvecia bassiana* ATCC 74040.

2. A biopesticidal composition comprising an effective amount of a fungus having the identifying characteristics of *Beauvecia bassiana* ATCC 74040 and an agriculturally acceptable carrier.

3. The composition of claim 2 wherein said fungus is in the form of spores.

4. The composition of claim 2 wherein the carrier is in the form of a liquid, a powder, granules or small particles.

5. The composition of claim 2 wherein the carrier is a liquid comprising water and a wetting agent.

6. The composition of claim 2 wherein the carrier comprises a cotton plant derivative.

7. The composition of claim 3 wherein the carrier is a liquid carrier having $2 \times 10^8$ to $2 \times 10^{14}$ spores of *Beauveria bassiana* per milliliter of carrier.

8. A biopesticidal composition for controlling a targeted pest comprising a fungus having the identifying characteristics of *Beauveria bassiana* ATCC 74040 and an arrestant and feeding stimulant for the targeted pest.

9. The composition of claim 8 further comprising a pheromone for the targeted pest.

10. The composition of claim 8 wherein said targeted pest is selected from the group consisting of boll weevil, cotton fleahopper, and sweet potato white fly.

11. The composition of claim 9 wherein the targeted pest is boll weevil and said composition contains boll weevil grandlure.

12. The composition of claim 8 wherein the feeding stimulant is a cotton derived feeding stimulant.

13. A process for controlling a pest selected from the group consisting of boll weevil, cotton fleahopper, and sweet potato white fly comprising applying the *Beauveria bassiana* of claim 1 to the pest, to foliage of plants or to soil around plants.

14. A process for controlling a pest selected from the group consisting of boll weevil, cotton fleahopper, and sweet potato white fly comprising applying the composition of claim 2 to the pest, to foliage of plants or to soil around plants.

15. A process for controlling a pest selected from the group consisting of boll weevil, cotton fleahopper, and sweet potato white fly comprising applying the composition of claim 8 to the pest, to foliage of plants or to soil around plants.

* * * * *